(12) United States Patent
Wittmann et al.

(10) Patent No.: US 11,612,690 B2
(45) Date of Patent: Mar. 28, 2023

(54) DRIVE APPARATUS FOR INJECTION DEVICES

(71) Applicant: Ypsomed AG, Burgdorf (CH)

(72) Inventors: Jürgen Wittmann, Burgdorf (CH); Markus Tschirren, Burgdorf (CH); Urs Klötzli, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 221 days.

(21) Appl. No.: 16/793,837

(22) Filed: Feb. 18, 2020

(65) Prior Publication Data

US 2020/0188592 A1 Jun. 18, 2020

Related U.S. Application Data

(63) Continuation of application No. PCT/IB2018/056478, filed on Aug. 27, 2018.

(30) Foreign Application Priority Data

Aug. 31, 2017 (CH) ..................................... 01079/17

(51) Int. Cl.
*A61M 5/20* (2006.01)
*A61M 5/31* (2006.01)
*A61M 5/315* (2006.01)

(52) U.S. Cl.
CPC ............ *A61M 5/20* (2013.01); *A61M 5/3129* (2013.01); *A61M 2005/202* (2013.01);
(Continued)

(58) Field of Classification Search
CPC ........... A61M 2005/31508; A61M 2005/3143; A61M 2005/31521
See application file for complete search history.

(56) References Cited

U.S. PATENT DOCUMENTS

| 5,094,148 A * | 3/1992 | Haber ............... A61M 5/31515 604/110 |
| 2010/0137801 A1* | 6/2010 | Streit .................. A61M 5/2033 604/138 |

(Continued)

FOREIGN PATENT DOCUMENTS

| DE | 102007013838 A1 | 9/2008 |
| WO | 2005115514 A1 | 12/2005 |

(Continued)

OTHER PUBLICATIONS

International Search Report and Written Opinion received for International Application No. PCT/IB2018/056478, dated Nov. 23, 2018, 15 pages.

(Continued)

*Primary Examiner* — Kevin C Sirmons
(74) *Attorney, Agent, or Firm* — Dorsey & Whitney LLP (57) ABSTRACT

An injection device includes: a housing with a product container in which a stopper with a bearing face can be moved to a stopper end position and which, proximally to the stopper end position, has a minimum product container cross section; a drive configured to move the stopper, which includes a plunger rod with a drive face that contacts the bearing face; a plunger rod guide is arranged outside the product container and guides the plunger rod, with a plunger rod guide cross section adapted to a plunger rod cross section. The product container only incompletely guides movement of the plunger rod and the plunger rod cross section is not prevented from moving in a tilting direction by the minimum product container cross section, and a plunger rod centering aid a distal end of the plunger rod limits the movement of the plunger rod in the tilting direction.

22 Claims, 7 Drawing Sheets

(52) U.S. Cl.
CPC .............. *A61M 2005/206* (2013.01); *A61M 2005/3132* (2013.01); *A61M 2005/3154* (2013.01)

(56) References Cited

U.S. PATENT DOCUMENTS

| | | | |
|---|---|---|---|
| 2011/0319835 A1* | 12/2011 | Burren | A61M 5/31535 |
| | | | 604/209 |
| 2013/0018328 A1* | 1/2013 | Jugl | A61M 5/31515 |
| | | | 604/220 |
| 2013/0204195 A1* | 8/2013 | Ekman | A61M 5/3158 |
| | | | 604/220 |
| 2016/0015901 A1 | 1/2016 | Plumptre | |

FOREIGN PATENT DOCUMENTS

| | | |
|---|---|---|
| WO | 2016042075 A1 | 3/2016 |
| WO | 2016205962 A1 | 12/2016 |
| WO | 2019043549 A1 | 3/2019 |

OTHER PUBLICATIONS

International Preliminary Report on Patentability issued in International application No. PCT/IB2018/056478, dated Mar. 3, 2019, 8 page.

* cited by examiner

DRIVE APPARATUS FOR INJECTION DEVICES

RELATED APPLICATION

This application is a continuation of International Patent Application No. PCT/IB2018/056478, filed Aug. 27, 2018, entitled "DRIVE APPARATUS FOR INJECTION DEVICES," which in turn claims priority to Swiss Patent Application No. 01079/17 filed Aug. 31, 2017, each of which is incorporated by reference herein, in their entirety and for all purposes.

TECHNICAL FIELD

The present invention relates to the field of medical injection devices for administering liquid substances, particularly drugs or medicinal substances such as insulin and hormone preparations. The invention relates to a space-saving drive apparatus with a plunger rod for advancing a stopper in the product container of an injection device.

BACKGROUND

Injection devices or injection units for the simplified administration of a substance include, amongst other things, so-called auto-injectors that have an energy storage or drive element, with which expulsion can be carried out automatically without any force applied externally or by a user. The energy storage or drive element beneficially stores all the energy needed to deliver the substance automatically in mechanical form. An example of such an energy storage or drive element is a spring, which is installed in the injection device in its compressed state and which can deliver energy by being released. The energy is beneficially delivered to a plunger rod or pressure element, which is able to insert a stopper into a product container. As an option, the energy storage or drive element may also be provided in order to automate the process of inserting an injection needle. Alternatively, a further, separate drive element may be provided for this purpose, or the insertion process takes place manually, in other words by a user, without using the energy stored for this purpose in the injection device.

The injection device may include a product container holder to accommodate a product container, where the product container can be held tightly and in particular axially and rotationally rigidly in the product container holder. The product container holder, axially and rotationally rigidly connected to the housing of the injection device, may be moved, relative to the housing, during an insertion and/or needle withdrawal process. The product container may be a carpule or a state-of-the-art prefilled syringe with a fixed injection needle. The product container comprises a hollow, cylindrical product container section, which movably supports a plunger or stopper. The plunger may form a sealing gap with the internal circumference of the product container section and can be displaced in a distal direction by means of a plunger rod in order to deliver product from the product container through the injection needle.

The injection device may have a needle protection sleeve, which, after injection, is positioned distally over the distal end of the injection needle or is moved into this position relative to the housing by releasing a needle protection sleeve spring in order to prevent accidental access to the injection needle and therefore reducing any risk of injury. In an auto-injector, the needle protection sleeve may also act as the triggering element to trigger release of the product, where the needle protection sleeve is moved in the proximal direction relative to the housing. Alternatively, the auto-injector can be released by operating a release button on the auto-injector, where the needle protection sleeve acts at least as visual protection before the auto-injector is used.

Patent application EP 2781230 describes an auto-injector for the automatic delivery of a medicinal substance by way of a pre-tensioned delivery or injection spring that presses a stopper into a pre-filled syringe via a plunger rod. The injection device also comprises a needle protection sleeve, which can be moved in a longitudinal direction between a proximal and distal position. The needle protection sleeve is connected to a needle protection sleeve spring as a separate drive element, and after the substance has been discharged, this spring forces the needle protection sleeve into the distal position, in which it encloses or screens off the needle at the side. A movable stop element, in the form of a feedback device to generate an acoustic signal following delivery of a specific quantity of substance, is accelerated toward a stop by the needle protection sleeve spring. A second feedback device with a stop element accelerated by the delivery spring signals the start of substance delivery. The needle protection sleeve spring is located in a proximal part of the auto-injector and encloses the plunger rod in the latter's starting position.

WO 2005/115514 A1 describes a drive element in the form of a plunger rod having a conical point at one distal end of the plunger rod facing the stopper, enclosed by an annular drive face. The plunger or stopper of a syringe has at its proximal end a center hole or recess with an internal thread, into which the tip of the plunger rod protrudes when dispensing. The hole in the stopper is enclosed by an annular bearing face, which makes contact with the drive face of the plunger rod during dispensing. A proximal rotationally-symmetrical opening in the syringe widens in the form of a funnel, and its internal surface has a minimal radius in a plane comprising the longitudinal axis. The combination of the plunger rod tip as centering aid and the rounded internal shape of the syringe makes it possible to compensate for or correct any inadequate axial alignment of plunger rod and syringe when introducing the latter into the proximal opening of the syringe. The maximum radial width of the circular drive face amounts, in any case, to less than one fifth of the total diameter of the plunger rod.

In the present context, the term "product," "medicament," or "medicinal substance" includes any fluid medicinal formulation, suitable for controlled administration by means of a cannula or hollow needle, for example a liquid, a solution, a gel, or a fine suspension containing one or more active medicinal substances. A product or medicament may therefore be a composition with a single active ingredient or a premixed or co-formulated composition containing several active ingredients from one single container. The term particularly includes medicines, such as peptides (e.g. insulins, insulin-containing medicaments, preparations containing GLP-1 as well as derived or analog preparations), proteins and hormones, biologically obtained or active substances, active substances based on hormones or genes, nutritional formulations, enzymes and other substances both in solid (suspended) or liquid form. The term also includes polysaccharides, vaccines, DNA or RNA or oligonucleotides, antibodies or parts of antibodies, as well as suitable base substances, excipients and carrier substances.

The term "distal" refers to the direction in which the point of the injection needle is pointing and the term "proximal" refers to the direction opposite the distal direction.

SUMMARY

An injection device according to the invention for administering a product comprises a housing to accommodate a product container having a product-receiving compartment to receive the product. In the product container, a stopper with a bearing face for dispensing the product from the product receiving compartment can be moved in the direction of a longitudinal axis of the injection device up to a stopper end position. Proximally in relation to the stopper end position at its narrowest point, the product container has a minimal product container cross section in a plane perpendicular to the longitudinal axis. The injection device also includes a drive in order to move the stopper, comprising a plunger rod with a cross section perpendicular to the longitudinal axis and a drive face on the stopper side, to drive the stopper by way of abutting, frictional contact with the latter's bearing face. The injection device also includes a plunger rod guide, located proximally in relation to the product container in the housing, with a guide cross section perpendicular to the longitudinal axis to guide the movement of the plunger rod in the direction of the longitudinal axis. The guide cross section is adapted to the plunger rod cross section or complementary to it, and limits any movement of the plunger rod cross section in all directions perpendicular to the longitudinal axis, to a manufacturing minimum. The product container itself guides the movement of the plunger rod in the direction of the longitudinal axis at best incompletely or asymmetrically, so that the plunger rod cross section is not prevented by the product container cross section from at least making a lateral movement in an initial tilting direction perpendicular to the longitudinal axis. At a distal end of the plunger rod, a plunger rod centering aid is provided in order to limit the movement of the plunger rod cross section into the initial tilting direction or to limit tilting of the plunger rod. As a result, the plunger rod centering aid also counteracts any rotational-symmetrical drive force distribution across the bearing face.

In a beneficial variant of the invention, a circular product container cross section with an initial diameter is assumed, where the geometrical considerations concerning the longitudinal guide of the plunger rod would have to be adapted differently, for example, for different oval cross section shapes. Likewise, circular guide and plunger rod cross sections with a second or third diameter would have to be beneficially assumed, where even angular, matched cross-sectional forms are conceivable, at least as long as the smallest circle surrounding the plunger rod cross section within the product container cross section has room. With the designations indicated, the first diameter is greater than the second and the latter in turn is no smaller than the third diameter. What is preferred is that the first diameter should be at least four or even seven percent larger than the third diameter. In another beneficial variant, the stopper has a central recess inside the bearing face, preferably a circular hole with an optional internal thread. Accordingly, the bearing face is preferably a circular face.

According to the invention therefore, a plunger rod with a maximum external diameter is used, which is preferably at least four percent smaller than the diameter of the product container. The resulting lost longitudinal guide of the plunger rod through the product container is compensated for by a centering aid at the tip of the plunger rod, which counteracts any imprecise or inadequate alignment of the plunger rod in the product container. In this way, space can be saved in the housing in the area of the plunger rod guide and the drive without the risk of any unforeseeable or even unsafe deviation in the alignment of the plunger rod from the longitudinal axis. The plunger rod centering aid is preferably made from the same inflexible material as the plunger rod.

In a first preferred embodiment of the injection device, the plunger rod centering aid comprises a centering flange to enlarge the plunger rod cross section. The centering flange therefore has a maximum flange diameter that is larger than a maximum external diameter of the plunger rod and smaller than a minimum internal diameter of the product container. From preference, the centering flange is positioned flush with the drive face so that the force transmission face is also enlarged in comparison with a plunger rod distal termination without a centering flange.

In a second preferred embodiment of the injection device, the plunger rod centering aid comprises a centering stub, in particular a conical or pyramidal stub. The centering stub has at its base a diameter that is smaller than the diameter of the hole in the stopper. The centering stub can be combined with the above-mentioned centering flange in a further, preferred embodiment.

The invention also relates to a drive for an injection device and a plunger rod for a drive for an injection device. To the expert, further embodiments and configurations that result from combinations of the examples described or combinations of the examples described coupled with the special technical knowledge of the expert are also directly and obviously apparent and within the scope of the present disclosure.

FIGURES

In connection with the attached figures, the following preferred embodiments of the invention are described. These are intended to highlight the fundamental potential of the invention and should in no way be interpreted as being restrictive.

The reference symbols and their meanings are summarized in the list of reference symbols. In general, the same reference symbols indicate the same parts.

DETAILED DESCRIPTION

Figure 1:
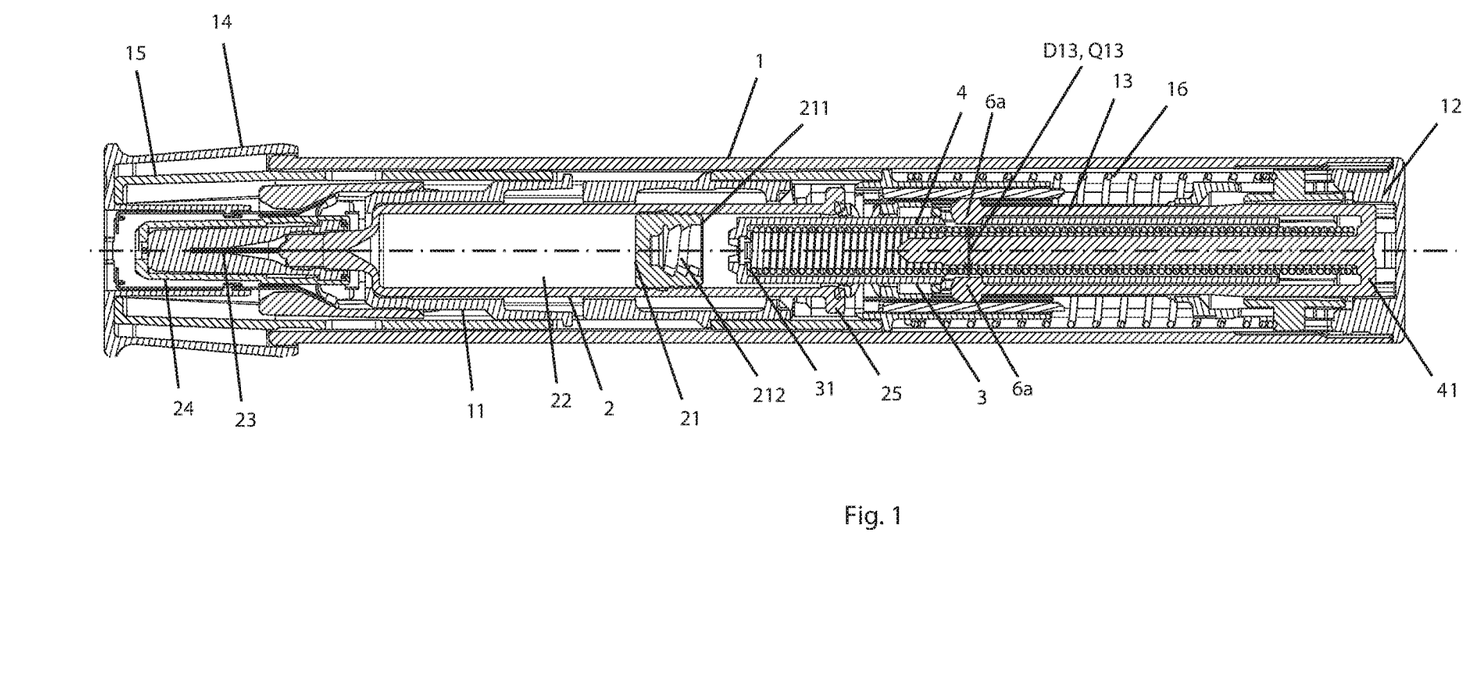
FIG. 1 shows a longitudinal section view of an injection device.

FIG. 1 shows a longitudinal sectional view of an injection device. The injection device comprises a sleeve-shaped, in particular, cylindrical housing 1, onto which is fitted a product container holder 11 and end cap 12. The product container holder 11 and end cap 12 can be firmly latched, glued, welded, locked or snapped onto the housing 1 or even be formed integrally with the housing 1 in each case, or in total. A product container 2 can be received in the product container holder 11 and held by it. The product container comprises a hollow cylindrical product receiving compartment 22, which is limited by a stopper 21 that can be moved along a longitudinal axis of the product container 2. During operation, the product receiving compartment 22 contains the product being dispensed, which can be forced out of the product receiving compartment 22 by moving the stopper 21 in a displacement direction from a stopper start position to a stopper end position. The stopper 21 has an annular bearing face 211 on a side facing away from the direction of displacement, said bearing face enclosing a center hole 212 or recess with an optional internal thread. The injection device also comprises a drive with a plunger rod 3 for moving the stopper 21 of the product container 2 in the direction of displacement. The plunger rod 3 is guided outside the product container 2 in the direction of the longitudinal axis by a plunger rod guide 13. For its part, the plunger rod guide 13 can be moved in the direction of the longitudinal axis and comprise a sleeve enclosing the plunger rod 3 and/or a mandrel enclosed by the plunger rod 3. The plunger rod guide 13 may, at the same time, take on the function of a holding element, which prevents any movement of the plunger rod 3 in the dispensing direction and holds an injection spring 4 in its tensioned state. For this purpose, the plunger rod guide 13 may have two flexible holding arms 6c with gripping elements 6a opposite one another, which initially engage in recesses 34 in the plunger rod 3. See FIGS. 6a and 7a. Following release, the plunger rod 3 slides along the flexibly mounted gripping elements 6a such that a diameter D13 of the cross section Q13 of the plunger rod guide 13 or linear extent is defined between the gripping elements 6a, said diameter being of the same size as a maximum diameter D3 of a cross section Q3 of the plunger rod 3 in the same direction (see D3 in FIGS. 3 and 5).

The preferred product container shown in FIG. 1 is a pre-filled syringe 2 made from glass or plastic, with a product receiving compartment 22 from which a product can be administered by displacing the stopper 21 in the distal longitudinal direction of the pre-filled syringe 2 (to the left in FIG. 1) by means of an injection needle 23 permanently connected to the front of the pre-filled syringe 2. The injection needle 23 in its initial state shown in FIG. 1 is enclosed by a needle protection cap 24, in which there is a flexible needle protection element made, for example, from TPE or rubber. The needle protection cap 24 can be withdrawn together with the needle protection element by means of a cap withdrawal element 14 placed on top of it, in order to expose the injection needle 23. The injection needle 23 is further enclosed by a needle protection sleeve 15, which is axially displaceably mounted relative to the housing 1 and can be inserted into the housing 1. At its distal front end, the needle protection sleeve 15 has an opening through which the injection needle 23 can penetrate when the needle protection sleeve and injection needle are moved relative to one another. The needle protection sleeve 15 can also act as a triggering element to start product dispensing, where the needle protection sleeve is displaced proximally for this purpose relative to the housing, with the needle protection sleeve spring 16 being under tension. At the proximal end of the pre-filled syringe 2, a flange 25 is located, which is also described as a finger flange.

The drive, illustrated in FIG. 1, also comprises an injection spring 4 or dispensing spring in the form of a compression spring, which acts as an energy store or drive means. The injection spring 4 preferably stores at least sufficient energy for completely dispensing the product in the product receiving compartment 22 and is inserted in the injection device as a pre-tensioned spring. The injection spring 4 is located inside the plunger rod 3 and is supported against a front terminal element 31 of the plunger rod. In the proximal direction, the injection spring 4 is held and supported during product dispensing by a proximal base or plate element 41. In FIG. 1, the base element 41 is integral with the plunger rod guide 13 and can be moved in a longitudinal direction in order to generate a start signal. Alternatively, the injection spring may take the form of a coil spring or torsion spring and/or also be responsible for moving the product container holder 11 in addition to dispensing product.

Figure 5:
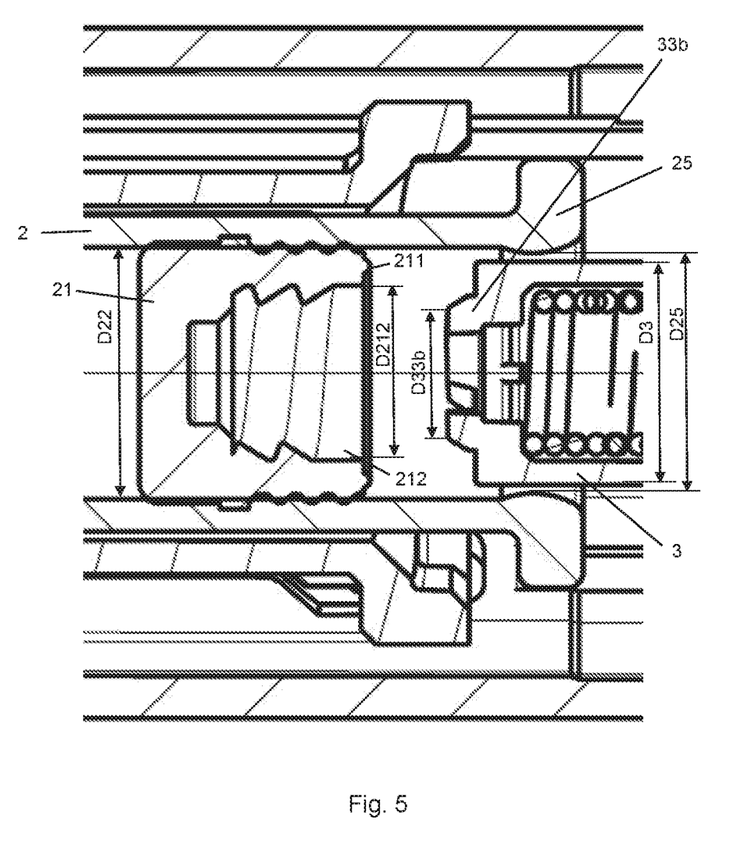
FIG. 5 shows a longitudinal section of the second embodiment.

In connection with a second embodiment of the invention described later, FIG. 5 shows an enlarged central section of FIG. 1. The product receiving compartment 22 has an internal diameter D22, where the product container 2 has an optional minimum internal diameter D25 close to the flange 25, which is smaller than the internal diameter D22 of the product receiving compartment 22. The plunger rod 3 in turn, has a cross section with a maximum diameter D3, which is smaller than the minimum internal diameter D25 and therefore also smaller than the internal diameter D22 of the product receiving compartment. The cross section of the plunger rod 3 may comprise edges, i.e. be designed as square or triangular, but should find space within a circle with a diameter that is smaller than the minimum internal diameter D25 of the product container, corresponding to the maximum diameter D3. The plunger rod cross section preferably and at least partially corresponds to an internal cross section of the plunger rod guide 13 (not shown in FIG. 5) in the proximal section of the housing. Therefore, product container 2, in the area penetrated by the tip of the plunger rod 3 and situated proximally to a stopper end position, has a minimum diameter that is at least four and preferably at least seven percent larger than the maximum diameter D3 of the plunger rod 3 and is therefore not suitable at least for guiding the plunger rod 3 precisely in the longitudinal direction. Instead, by selecting a narrow plunger rod 3 in the proximal part of the housing 1 adjoining the flange 25, space can be created for additional concentric components, such as the needle protection sleeve spring 16, or existing components can likewise be configured with a smaller diameter, thereby reducing the overall diameter of the device.

When the plunger rod 3 is exclusively guided outside the product container 2, an imprecise or insufficient axial alignment of the plunger rod 3 in the product container 2 can no longer be completely ruled out. Tilting or deviation from the longitudinal axis, which the plunger rod 3 may still be able to sustain in contact with the stopper 21 following introduction into the product container 2, is limited to a few degrees as a result of the geometries involved. In spite of this, as a result of asymmetric support of the plunger rod tip on the stopper 21, the driving force is concentrated on a section of the annular drive force transmission surface of the stopper 21 and is therefore locally increased. Particularly in the case of large forces, for example with a highly viscous delivery product, this may result in unilateral compression, pinching or even jamming of the stopper 21, or to the wall of the hole yielding and forming a radial internal bulge. Such uncertain and unforeseen situations can, in the end, lead to an axially imprecisely defined end position of the plunger rod. To remedy this, a centering aid is provided at a distal end of the plunger rod 3 to prevent the plunger rod 3 moving in a tilting direction and to even out any distribution of drive force across the annular bearing face 211. The centering aid can be permanently latched, glued, welded, locked, or snapped onto the plunger rod 3, or even configured as an integral part of the plunger rod 3.

Figure 2:
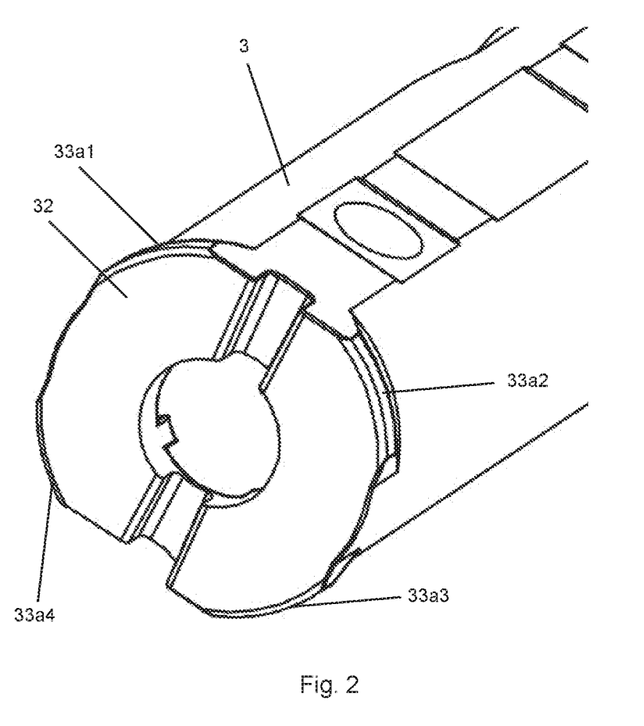
FIG. 2 shows an isometric view of a first embodiment with a centering flange.
Figure 3:
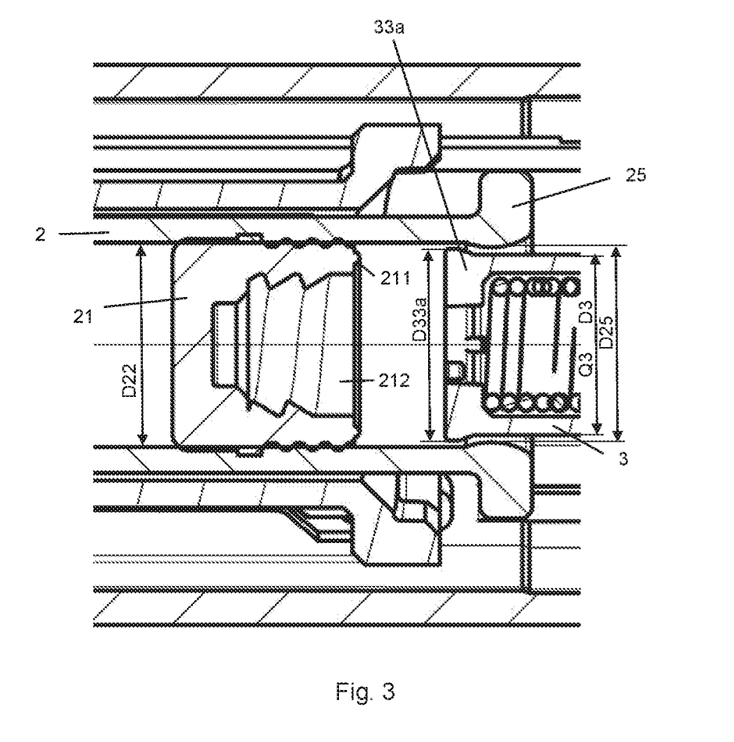
FIG. 3 shows a longitudinal section of the first embodiment.

FIGS. 2 and 3 show an isometric top view and longitudinal section of a first embodiment of the invention with the plunger rod center ring or guide aid in the form of a centering flange 33a that protrudes laterally or radially beyond the plunger rod 3. A cross section of the centering flange 33a perpendicular to the longitudinal axis has a maximum flange diameter D33a or maximum linear extent that is no larger than the minimum internal diameter D25 of the product container 2, but is larger than the maximum diameter D3 of the cross section of the plunger rod 3. The centering flange 33a improves the guidance of the plunger rod 3 in the product container 2 in comparison with a plunger rod tip with unchanged cross section.

In the variant of the first embodiment, the centering flange 33a is not entirely circular for manufacturing reasons, but is divided into a number of arc segments of maximum radial extent distributed over the circumference. FIG. 2 shows four such flange segments 33a1 to 33a4, which are offset against each other by 90° and also run out at their tangential end in such a way that they find space in a square, the side length of which is equal to the plunger rod diameter D3. The drive face 32 is in the shape of an annulus, which is interrupted by a diagonal recess. The centering flange 33a shown contributes to a radial enlargement of the drive face 32, or it can alternatively be set back a small distance in a proximal direction from the drive face 32, without losing its centering effect as a result.

A narrow plunger rod 3 without a guide in the product container is of particular importance for product containers with a volume of more than 1 ml and preferably 2.25 ml and duly adapted minimum internal diameter. For a pre-filled syringe with a 2.25 ml volume, the internal diameter D22 (see e.g., FIG. 3) is 8.65±0.1 mm and the minimum internal diameter D25 (see e.g., FIG. 3) is at least 8.25 mm for a plunger rod diameter D3 of 7.65±0.1 mm and a flange ring width of 0.225 mm, and this results in a maximum flange diameter D33a of 8.1 mm, which is slightly less than the minimum internal diameter D25. The diameter of the plunger rod guide 13 measures 7.9±0.1 mm and is therefore distinctly smaller than the minimum internal diameter D25 of the product container 2.

Figure 4:
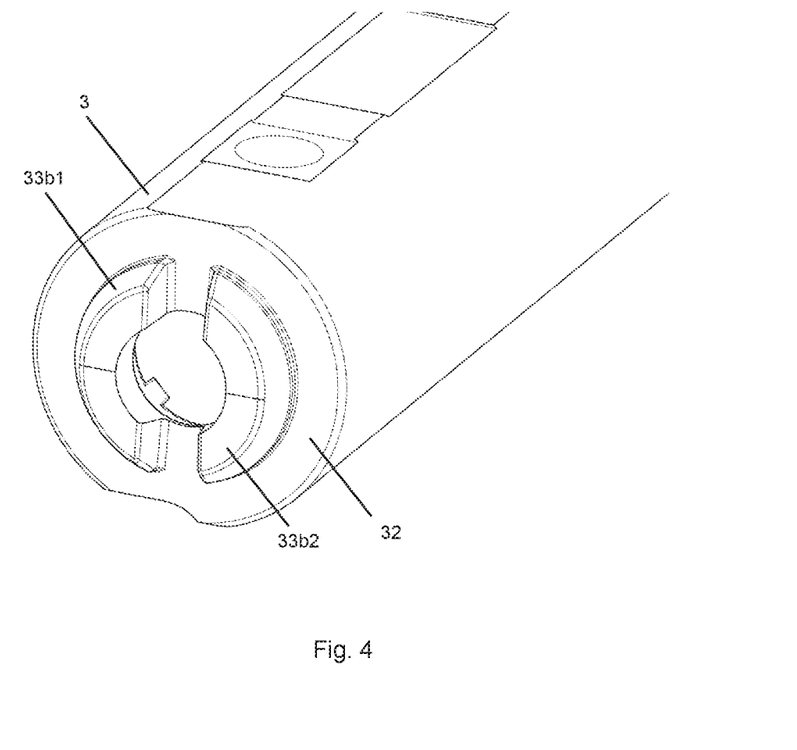
FIG. 4 shows an isometric view of a second embodiment with a centering cone.

FIGS. 4 and 5 show an isometric top view and a longitudinal section, respectively, of a second embodiment of the plunger rod centering aid in the form of a centering stub 33b. The centering stub 33b is located within the annular drive face 32 and, at its base, has a base diameter that is less than the diameter D212 of the hole 212 in the stopper 21. The centering stub 33b shown has an advantage over a pointed cone in that wherein a minimum distance has to be guaranteed between the stopper (bearing face 211) and plunger rod tip in its initial position, the plunger rod 3 has to be displaced less forcibly in the proximal direction. For this purpose, the height of the centering stub 33b is preferably less than half, particularly less than one quarter of the depth of the hole 212 in the stopper 21. At its tip, the centering stub has a diameter D33b of at least one quarter and preferably at least half the diameter D3 of the plunger rod.

Instead of the conical stub with circular base shown in FIGS. 4 and 5, a pyramidal stub with an angular, in particular at least square, base face as centering stub is also possible. The centering stub may also be composed of several segments; in FIG. 4, for example, it is divided into two parts 33b1, 33b2 by a diagonal recess. As a result of the limited deviation from the maximum three degrees from the longitudinal axis, at which the plunger rod can strike the stopper after introduction into the product container, the flank pitch of the centering stub, which must be no less than the deviation quoted, may also turn out to be correspondingly modest. The flank of the centering stub is used to center the plunger rod when it first makes contact with the edge of the stopper hole and then with the base of the stub during product discharge for improved guidance of the plunger rod in the product container.

In FIG. 9ff of patent application WO 2016/205962, the entire content of the application incorporated by reference herein in its entirety, an auto-injector is described, which comprises a housing with longitudinal axis, a release mechanism, a product container secured axially in the housing, in particular in the form of a pre-filled syringe or carpule, where, in the product container, an axially displaceable stopper is located, through which product can be dispensed from the product container when the stopper is displaced in a distal direction. A torsion, coil or motive spring in which energy can be stored for the automatic dispensing of product, is connected to the release mechanism, wherein an initial end of the torsion spring is connected to the housing and a second end of the torsion spring is connected in the fixed position to a threaded rod located co-axially to the longitudinal axis. A two- or multi-part plunger rod includes at least one outer plunger rod, which does not rotate in the housing and which is in the shape of a sleeve and, when displaced in the distal direction, also moves the product container stopper in the distal direction. The two- or multi-part plunger rod also includes at least one inner plunger rod, which is at least partially mounted inside the outer plunger rod and can transmit forces to the latter in a distal direction. At its proximal end, the inner plunger rod has a guide element, which may be engaged in a longitudinal guide or rib of the housing and is connected to the threaded rod through a threaded connection, so that during discharge of the product, the result is a rotary movement of the threaded rod in an axial movement of the inner plunger rod.

The outer and inner plunger rod together define a cavity with an inner volume, which is at least partially filled with a viscous fluid or a gelatinous or fatty substance, so that given a relative rotation between inner and outer plunger rod, the viscous fluid develops a resistance to displacement. The internal volume of the cavity may be defined as a gap between a section of the outer surface of the inner plunger rod and a section of the inner surface of the outer plunger rod. Alternatively, the cavity may also be located at the distal end of the inner plunger rod and be of roughly cylindrical shape. In both cases, rudder-like fluid displacement structures, which are firmly connected to at least the inner plunger rod, protrude into the cavity or into the viscous fluid.

When delivering, the inner plunger rod shall be initially guided by the guide element in a way that it cannot be twisted but can be moved. Only after the inner plunger rod has been moved a certain distance distally is the guide element released by the longitudinal guide of the housing and, under the effect of the torque of the threaded rod, the inner plunger rod starts to rotate. The viscous fluid slows the rotation of the inner plunger rod and any possible fluid displacement structures connected to it such that they cannot be twisted and are submerged in the viscous fluid. In particular, the rotation of these structures causes the viscous fluid to be forced out of an initial chamber through an opening, into a second chamber, thereby generating pressure and friction and slowing down rotation.

At its proximal end, the inner plunger rod has at least one release structure protruding in a radial direction and in particular at least one indentation is able to release a release structure depending on the indentation's orientation relative to the longitudinal axis. As soon as the slowed rotation of the inner plunger rod has achieved a pre-determined orientation, the release structure is released and a delayed end signal produced.

The proximal end of the inner plunger rod preferably forms an annular structure or a flange with an enlarged external diameter. This annular structure is interrupted by one or more recesses or indentations, which act as a guide element as protection against twisting in relation to the longitudinal guide of the housing and/or to release the holding element on completion of product dispensing. The recesses distributed over the circumference of the annular structure can therefore be of double use depending on the arrangement of longitudinal guide and holding element and the delaying characteristics of the viscous fluid. If, for example, the holding element in its holding state is displaced somewhat distally from a distal end of the longitudinal guide and by 90° in relation to it, the inner plunger rod can perform a gentle quarter turn in order to delay the end signal.

In other words, the plunger rod centering aid formed according to the invention may also be the distal end of an external plunger rod that defines a cavity as part of a delaying mechanism on its inside in order to receive a viscous fluid as described above and disclosed in detail in WO 2016/205962.

Figure 6A:
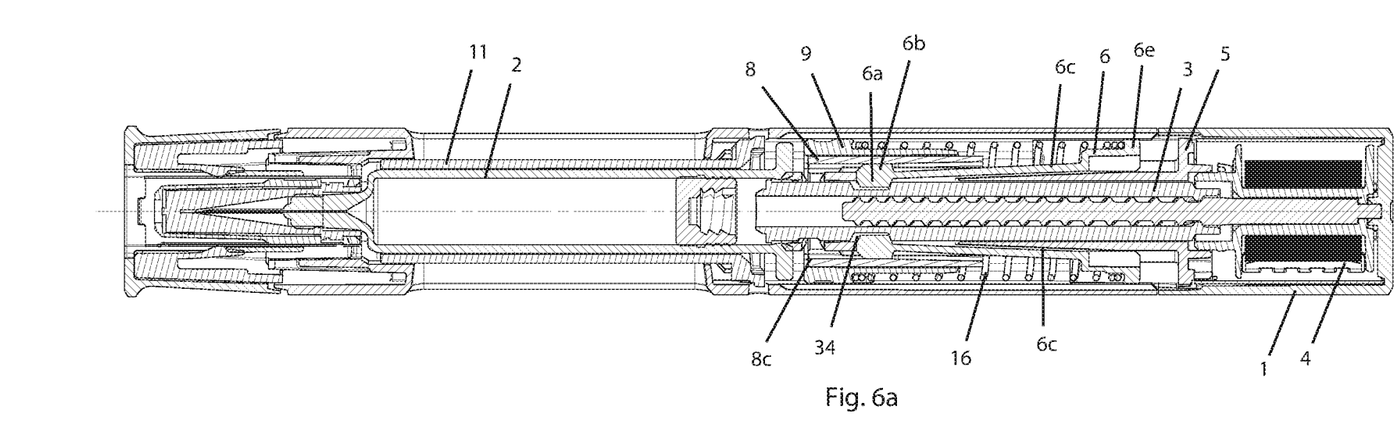
FIGS. 6a and 6b show two longitudinal sectional views of an auto-injector in its initial state.
Figure 6B:
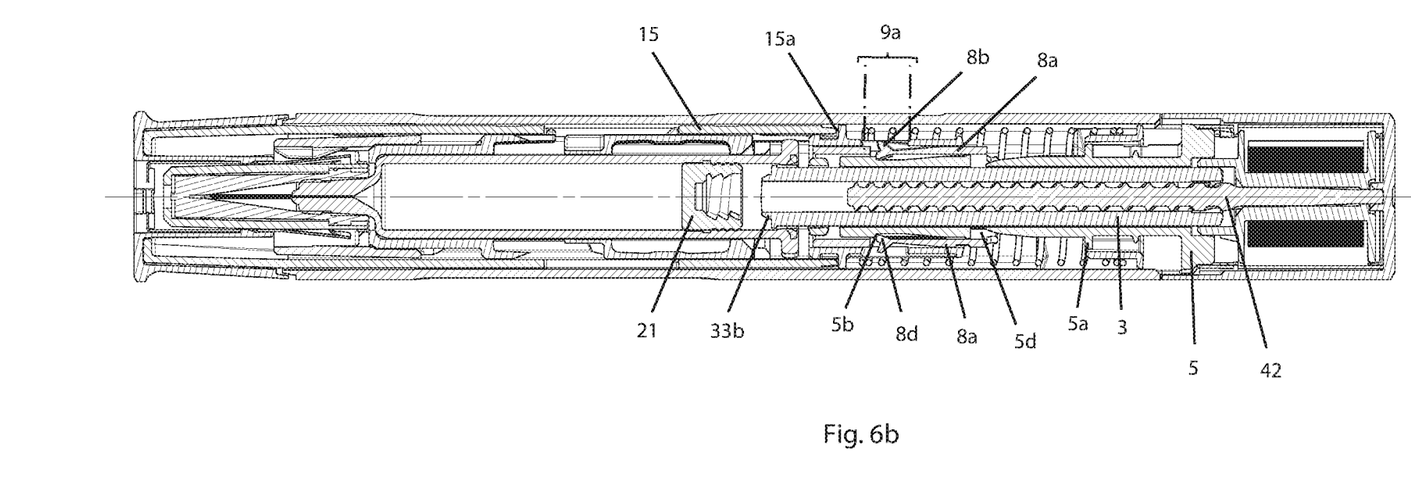

FIGS. 6a and 6b of the present disclosure show two longitudinal section views, offset by approximately 90°, of a further embodiment of an auto-injector in its initial state or state of delivery. The auto-injector has a holding element 6 with two holding arms 6c, wherein a first engaging element 6a and a second engaging element 6b are positioned on each holding arm 6c. The first engaging element 6a points radially to the longitudinal axis L, where the second engaging element 6b points radially away from the longitudinal axis L. The first engaging element 6a engages in a recess 34, formed by the plunger rod 3, thereby preventing any movement of the plunger rod 3 relative to the holding element 6 in the dispensing direction, and holding an injection spring 4 or ejection spring in the form of a torsion spring in its tensioned state and preventing rotation of the threaded rod 42 threadedly connected to the plunger rod 3.

The auto-injector has a control module 8, 9, which has a control sleeve 9 and a locking sleeve 8 that can be moved axially in relation to the control sleeve 9 and is at least partially enclosed by the control sleeve 9. Therefore the control module 8, 9 forms a telescopic mechanism with an outer telescopic control sleeve 9 and an inner telescopic locking sleeve 8. In its delivered state, the first engaging element 6a of the device is held in the engagement with the recess 34 by the internal circumference of the locking sleeve 8, which is adjacent to the second engaging element 6b.

The control sleeve 9 is located at a proximal end 15a of the needle protection sleeve 15. A needle protection spring 16, which preferably at least partially encloses the control sleeve 9 and locking sleeve 8, is supported at its distal end by the control sleeve 9. Part of the control sleeve 9 is therefore located between the needle protection sleeve 15 and the distal end of the needle protection spring 16. The needle protection spring 16 is a metal spring that acts as a compression spring and is configured as a coil spring. The needle protection spring 16 is supported at its proximal end by a protrusion 6e of the holding element 6, which engages in the housing 1 such that it is axially displaceable and is rigid. The needle protection spring 16 therefore also encloses, at least partially and preferably completely, a mechanism holder 5, which is connected to the housing in such a way that it cannot rotate and is axially fixed.

The control sleeve 9 has a recess or opening 9a with an axial length or extent, which is limited in the axial direction by a distal and proximal limit, each in the form of an edge or frame section. A saw-tooth shaped locking member 8b of the locking sleeve 8, which is directed outward and radially from the longitudinal axis L, engages in the recess 9a from inside. The locking member 8b, which is flexibly located preferably on a distally orientated locking arm 8a, which is formed by the locking sleeve 8, is preferably connected to the locking sleeve 8 by its proximal end so as to be axially rigid. By moving the needle protection sleeve 15 into the actuated position, the control sleeve 9 is pushed in the proximal direction, thereby also taking with it, or pushing, the locking sleeve 8 by way of the engagement of the blocking member 8b, with a distal limit of the recess 9a in the proximal direction. The locking member 8b can move axially within and opposite the recess 9a, between the distal and proximal limit, by a maximum distance of the axial length of the recess 9a of the control sleeve 9. In the initial state, a location recess or indentation 5b in the mechanism holder 5 can ensure that a locking member 8d on the inside of the locking arm 8a holds the locking member 8b within the recess 9a, and therefore the whole locking sleeve 8, in a desired axial position. The proximal limit of this recess 5b is designed in such a way, and in particular is tapered, so that the locking member 8d can slide with low resistance in the proximal direction during an actuating movement. The location recess 5b in FIG. 6 is axially extended so that any movement of the locking sleeve 8 in its initial state is completely or unilaterally limited by the recess 9a in the control sleeve 9 and the locking member 8b engaging in it but not or at most unilaterally by the recess 5b in the mechanism holder 5. Alternatively, the location recess 5b may have a minimal axial extent and can axially pinpoint the locking sleeve 8.

The locking sleeve 8 has a distal end 8c, which is brought to the position of the second engagement element 6b when the auto-injector is actuated or applied by sliding the control sleeve 9 by an actuation stroke larger than a maximum distance of the opening 9a of the control sleeve 9 along the longitudinal axis L. As a result, the first engagement element 6a is moved out of engagement with the plunger rod 3 by a movement perpendicular to the longitudinal axis L, where at the same time the second engagement 6b ends up in the engagement with the distal end 8c of the locking sleeve 8. As a result, the plunger rod 3 is released to move in the dispensing direction by the size of the dispensing stroke. Following release, the mechanism holder 5 acts as a plunger rod guide to guide any movement of the plunger rod 3 in the direction of the longitudinal axis. The rigid cross section of the mechanism holder 5 is adapted as a guide cross section to the plunger rod 3 cross section, and is preferably slightly larger than the latter on all sides and limits any movement of the plunger rod cross section in all directions perpendicular to the longitudinal axis to a manufacturing minimum.

As the axially rigid coupling between the plunger rod 3 and the holding element 6 is now removed, the holding element, which can be moved at least to a certain extent relative to the housing 1 and along the longitudinal axis L, can be moved by the needle protection spring 16 in the proximal direction. By the engagement of the second engagement element 6b behind the distal end 8c of the locking sleeve 8, the latter is also moved by the accelerating holding element by a starting signal stroke, until the locking sleeve 8 strikes against a starting signal stop 5a, which is formed by the mechanism holder 5, thereby emitting an acoustic and/or tactile signal, which signals to the user of the device that dispensing of the product has started. During this signal movement, the locking sleeve 8 is moved by less than the length of a maximum distance of the opening 9a of the control sleeve 9 so that the locking member 8b does not strike the proximal limit of the recess 9a.

Figure 7A:
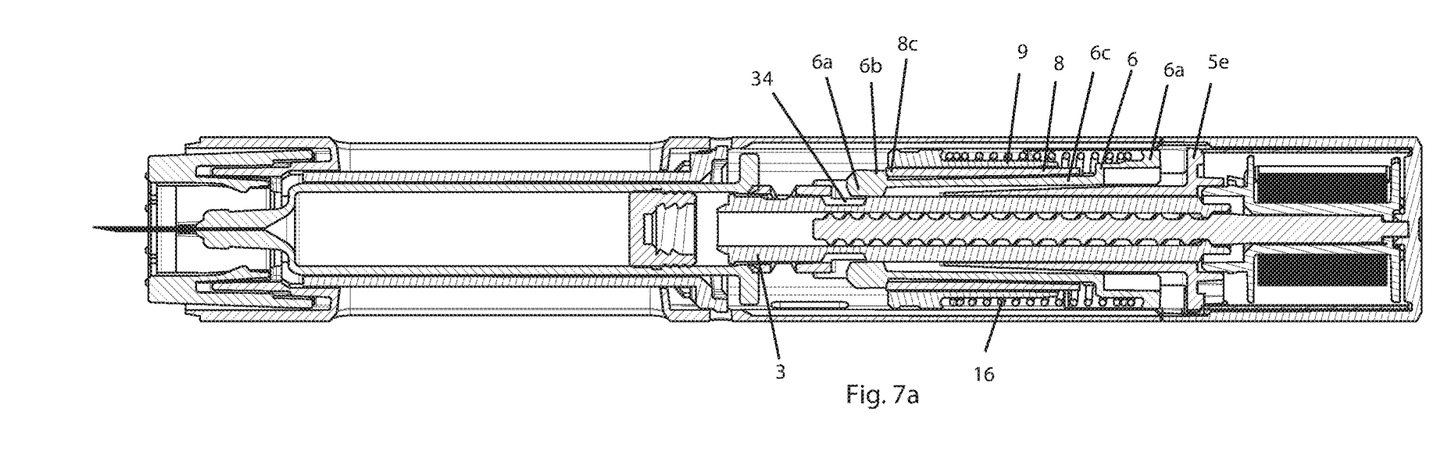
FIGS. 7a and 7b show two longitudinal sectional views of the auto-injector in its released state.
Figure 7B:
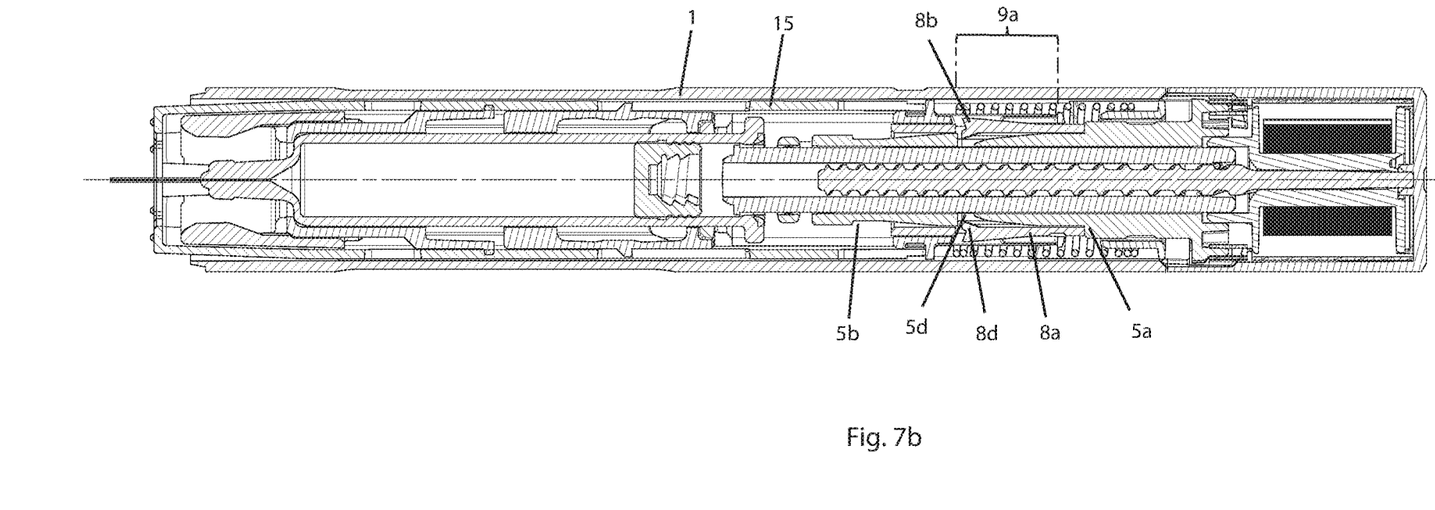

FIGS. 7a and 7b show two longitudinal section views, offset by 90°, of the further embodiment of an auto-injector in its state following start signaling and with activated needle protection. By moving the locking sleeve 8 via the starting signal stroke, the locking member 8d, which is mounted on locking arm 8a of the locking sleeve opposite the locking member 8b and protrudes in a saw-tooth shape radially inward or toward the longitudinal axis L, is released for a movement across and toward the longitudinal axis L and into a recess 5d of the mechanism holder 5. Thus, the locking member 8d can escape and snap into the recess 5d before the locking sleeve 8 impacts as a result of appropriate pre-tensioning of the locking arm 8a, without the locking member 8b coming out of the recess 9a. As a result, the locking sleeve 8 is rigidly connected to the mechanism holder 5, and any movement of the locking sleeve 8 in the distal direction relative to the housing 1 is prevented and a needle protection mechanism activated. In this position, the locking arm 8a is unstressed, i.e. is not tensioned radially either inward or outward.

As the second engagement member 6b is still located at the distal end 8c of the locking sleeve 8, this prevents the holding element 6 from moving further in the proximal direction relative to the housing 1 or the locking sleeve 8. The second engagement member 6b is held by the external circumference of the plunger rod 3 in the engagement with the locking sleeve 8 as long as the plunger rod 3 is moved by its dispensing stroke.

At the end of the dispensing stroke, the plunger rod 3 releases the first engagement member 6a for a movement particularly toward the longitudinal axis L, whereby the second engagement member 6b is moved out of engagement with the locking sleeve 8 such that the needle protection spring 16 accelerates the holding element 6 against the direction of dispensing, i.e., in the proximal direction, so that when the holding element 6 makes contact with the end signal stop 5e, an acoustic and/or tactile signal is generated.

By removing the auto-injector from the injection site, the needle protection spring 16 can move the control sleeve 9 and the needle protection sleeve 15 out of the actuated position into the needle protection position via the needle protection stroke, wherein the locking arm 8a is forced out of engagement with the recess 9a and the control sleeve 9 moves in the distal direction relative to the locking sleeve 8. If the needle protection sleeve 15 is in its needle protection position, the locking arm 8a snap-fits with the control sleeve 9 and the locking arm 8a prevents any renewed pushing back of the needle protection sleeve 15 to its actuated position. If an attempt is made to push the needle protection sleeve 15 back out of the needle protection position into the actuated position, the control sleeve 9 strikes the locking arm 8a, which prevents the movement of the needle protection sleeve 15 into the actuated position. For this purpose, the locking sleeve 8 is supported axially against the starting signal stop 5a of the mechanism holder 5.

LIST OF REFERENCE NUMBERS

1 Housing
11 Product container holder
12 End cap
13 Plunger rod guide
14 Cap removal element
15 Needle protection sleeve
15a Proximal end
16 Needle protection sleeve spring
2 Product container
21 Stopper
211 Bearing face
212 Hole
22 Product receiving chamber
23 Injection needle
24 Needle protection cap
25 Flange
3 Plunger rod
31 Termination element
32 Drive face
33 Plunger rod centering aid
33a Centering flange
33b Centering stub
34 Recess
4 Injection spring
41 Base element
42 Threaded rod
5 Mechanism holder
5a Starting signal stop
5b Location recess
5d Indentation
5e End signal stop
6 Holding element
6a First engagement element
6b Second engagement element
6c Holding arm
6e Protrusion
8 Locking sleeve
8a Locking arm
8b Locking member
8c Distal end
8d Locking member
9 Control sleeve
9a Recess

What is claimed is:

1. An injection device for administering a liquid product, comprising:
a housing configured to receive a product container in which a stopper with a bearing face to dispense the product can be moved in along a longitudinal axis of the injection device to a stopper end position and which, proximally to the stopper end position, has a minimum product container cross section;
a drive configured to move the stopper, the drive comprising a plunger rod with a drive face configured to contact the bearing face, the plunger rod comprising a plunger rod cross section and configured to move axially and non-rotatably; and
a mechanism holder configured as a plunger rod guide arranged outside the product container, wherein the mechanism holder is configured as a sleeve and arranged within the housing in a non-movable, axially fixed manner and an internal sidewall of the sleeve includes an internal cross-section configured to receive an external cross-section of the plunger rod and guide a non-rotational, axial movement of the plunger rod along the longitudinal axis, such that the plunger rod is slidably guided by the internal sidewall of the mechanism holder during the movement of the plunger rod along the longitudinal axis,
wherein the product container only incompletely guides the movement of the plunger rod along the longitudinal axis such that the plunger rod cross section is not prevented from moving in a tilting direction by the minimum product container cross section, wherein a plunger rod centering aid is provided at a distal end of the plunger rod to limit the movement of the plunger rod in the tilting direction, wherein the plunger rod centering aid comprises a centering flange having a maximum flange diameter that is larger than a maximum external diameter of the plunger rod and smaller than a minimum internal diameter of the product container, and wherein a holding element is configured as another plunger rod guide arranged outside the product container, wherein the holding element can be moved along the longitudinal axis relative to the plunger rod, and wherein the holding element comprises gripping elements configured to engage with the plunger rod to prevent movement of the plunger rod in the dispensing direction.

2. The injection device according to claim 1, wherein the minimum product container cross section is a circle with a diameter, the plunger rod cross section is a circle with a diameter, and the guide cross section is a circle with a diameter, wherein the diameter of the guide cross section is smaller than the diameter of the minimum product container cross section and greater than or equal to the diameter of the plunger rod cross section, and wherein the diameter of the minimum product container cross section is at least four percent larger than the diameter of the plunger rod cross section.

3. The injection device according to claim 2, wherein the bearing face of the stopper comprises an annular shape and encloses a hole in the stopper.

4. The injection device according to claim 1, wherein the centering flange contacts the bearing face.

5. The injection device according to claim 1, wherein the plunger rod cross section is accommodated in a circle with a diameter, and wherein the centering flange has a cross section that fits into a square with a side length of the diameter of the plunger rod cross section.

6. The injection device according to claim 1, wherein the drive configured to move the stopper comprises a compression spring as an energy store acting against a distal termination element of the plunger rod.

7. The injection device according to claim 1, wherein the drive configured to move the stopper comprises a torsion spring, which acts on a threaded rod, the threaded rod threadedly connected to the plunger rod, wherein the torsion spring is mounted rigidly in the housing at an initial end and is mounted to the threaded rod at a second end.

8. The injection device according to claim 7, wherein the drive further comprises an inner plunger rod connected by a threaded connection to the threaded rod and the plunger rod is configured as an outer plunger rod, wherein the inner plunger rod and the outer plunger rod together form a cavity that can be filled with a viscous fluid in order to attenuate any rotary movement of the inner plunger rod relative to the outer plunger rod.

9. The injection device according to claim 1, wherein the injection device is an auto-injector and the product container is a pre-filled syringe with a fixed injection needle and a normal filling capacity of 2.25 ml.

10. The injection device according to claim 1, wherein the product has a high viscosity of at least 5, preferably at least 15 cP (0.015 kgm$^{-1}$s$^{-1}$).

11. The injection device according to claim 1, wherein the centering flange is positioned flush with the drive face such that the centering flange and drive face define a flat surface.

12. The injection device according to claim 11, wherein the centering flange comprises radially extending arc segments distributed over a circumference of the drive face.

13. The injection device according to claim 11, wherein each of the arc segments are offset from each other by about 90°.

14. The injection device according to claim 11, wherein the drive face is interrupted by a diagonal recess.

15. The injection device according to claim 14, wherein the plunger rod is sleeve-shaped and wherein at least a portion of the diagonal recess defines an opening in the plunger rod centering aid extending to an interior of the sleeve-shaped plunger rod.

16. An injection device for administering a liquid product, comprising:

a housing configured to receive a product container in which a stopper with a bearing face to dispense the product can be moved in along a longitudinal axis of the injection device to a stopper end position and which, proximally to the stopper end position, has a minimum product container cross section;

a drive configured to move the stopper, the drive comprising a plunger rod with a drive face configured to contact the bearing face, the plunger rod comprising a plunger rod cross section;

a plunger rod guide arranged outside the product container and configured to guide a movement of the plunger rod along the longitudinal axis, the plunger rod guide comprising a guide cross section adapted to the plunger rod cross section, wherein the guide cross section is adapted to limit movement of the plunger rod cross section in all directions perpendicular to the longitudinal axis such that the plunger rod can only move axially and can not rotate around the longitudinal axis, wherein the plunger rod comprises an internal thread in a threaded connection with an external thread of a threaded rod and wherein rotation of the threaded rod moves the plunger rod along the longitudinal axis, wherein the product container only incompletely guides the movement of the plunger rod along the longitudinal axis such that the plunger rod cross section is not prevented from moving in a tilting direction by the minimum product container cross section, and wherein a plunger rod centering aid is provided at a distal end of the plunger rod to limit the movement of the plunger rod in the tilting direction.

17. The injection device according to claim 16, wherein the plunger rod centering aid comprises a centering flange having a maximum flange diameter that is larger than a maximum external diameter of the plunger rod and smaller than a minimum internal diameter of the product container.

18. The injection device according to claim 16, wherein the drive comprises a torsion spring, which acts on a threaded rod, the threaded rod threadedly connected to the plunger rod, wherein the torsion spring is mounted rigidly in the housing at an initial end and is mounted to the threaded rod at a second end.

19. The injection device according to claim 16, wherein the bearing face of the stopper comprises an annular shape and encloses a hole in the stopper.

20. An injection device for administering a liquid product, comprising:

a housing configured to receive a product container in which a stopper with a bearing face to dispense the product can be moved in along a longitudinal axis of the injection device to a stopper end position and which, proximally to the stopper end position, has a minimum product container cross section;

a drive configured to move the stopper, the drive comprising a plunger rod with a drive face configured to contact the bearing face, the plunger rod comprising a plunger rod cross section;

a plunger rod guide arranged outside the product container and configured as a sleeve and arranged within the housing in a non-movable, axially fixed manner, the plunger rod guide comprising an internal sidewall including an internal cross-section configured to receive an external cross-section of the plunger rod so as to guide a movement of the plunger rod along the longitudinal axis as the plunger rod slides along the internal sidewall of the plunger rod guide, wherein the product container only incompletely guides the movement of the plunger rod along the longitudinal axis such that the plunger rod cross section is not prevented from moving in a tilting direction by the minimum product container cross section, and wherein a plunger rod centering aid is provided at a distal end of the plunger rod to limit the movement of the plunger rod in the tilting direction, wherein the centering aid is a centering flange enlarging the plunger rod cross section, and wherein the centering flange has a maximum flange diameter that is larger than a maximum external diameter of the plunger rod and smaller than a minimum internal diameter of the product container, and wherein the centering flange is positioned flush with the drive face of the plunger rod and does not include a stub or a recess matched to the bearing face of the stopper.

21. The injection device according to claim 20, wherein the drive comprises a torsion spring, which acts on a threaded rod, the threaded rod threadedly connected to the plunger rod, wherein the torsion spring is mounted rigidly in the housing at an initial end and is mounted to the threaded rod at a second end.

22. The injection device according to claim 20, wherein the bearing face of the stopper comprises an annular shape and encloses a hole in the stopper.

* * * * *